(12) United States Patent
Schetz et al.

(10) Patent No.: US 8,895,637 B2
(45) Date of Patent: Nov. 25, 2014

(54) ENVIRONMENT-FRIENDLY ANTIFOULANTS FOR THE PREVENTION OF BIOFOULING

(71) Applicants: University of North Texas Health Science Center at Fort Worth, Fort Worth, TX (US); The Board of Regents of the University of Texas System, Austin, TX (US)

(72) Inventors: John A. Schetz, Fort Worth, TX (US); Robert F. McMahon, Arlington, TX (US)

(73) Assignees: University of North Texas Health Science Center at Fort Worth, Fort Worth, TX (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/063,568

(22) Filed: Oct. 25, 2013

(65) Prior Publication Data

US 2014/0051751 A1 Feb. 20, 2014

Related U.S. Application Data

(62) Division of application No. 12/595,997, filed as application No. PCT/US2008/004891 on Apr. 16, 2008, now Pat. No. 8,575,230.

(60) Provisional application No. 60/925,260, filed on Apr. 19, 2007.

(51) Int. Cl.
| | |
|---|---|
| *A01N 43/16* | (2006.01) |
| *A01N 43/84* | (2006.01) |
| *A01N 31/08* | (2006.01) |
| *A01N 31/14* | (2006.01) |
| *A01N 37/18* | (2006.01) |
| *A01N 37/20* | (2006.01) |
| *A01N 37/42* | (2006.01) |
| *A01N 37/50* | (2006.01) |
| *C09D 5/16* | (2006.01) |

(52) U.S. Cl.
CPC ............... *A01N 43/84* (2013.01); *A01N 31/14* (2013.01); *A01N 37/50* (2013.01); *A01N 37/20* (2013.01); *C09D 5/1625* (2013.01); *A01N 31/08* (2013.01); *A01N 37/18* (2013.01); *A01N 37/42* (2013.01); *A01N 43/16* (2013.01)
USPC ......................................................... 523/122

(58) Field of Classification Search
USPC .......... 523/122; 514/454, 534, 625, 627, 734; 544/143; 560/106; 564/151, 192, 207, 564/208; 568/675, 743; 549/390
See application file for complete search history.

(56) References Cited

U.S. PATENT DOCUMENTS

| | | | | |
|---|---|---|---|---|
| 5,397,385 | A | * | 3/1995 | Watts .......................... 106/18.32 |
| 5,629,045 | A | * | 5/1997 | Veech ........................... 427/297 |
| 6,306,506 | B1 | | 10/2001 | Timmons et al. |
| 6,607,826 | B1 | * | 8/2003 | Hatch ........................... 428/343 |
| 2005/0080160 | A1 | | 4/2005 | Seabrook, Jr. |

FOREIGN PATENT DOCUMENTS

| | | |
|---|---|---|
| WO | 2005/025314 A1 | 3/2005 |
| WO | 2005/027642 A1 | 3/2005 |

OTHER PUBLICATIONS

Cope, W.G., et al; Efficacy of Candidate Chemicals for Preventing Attachment of Zebra Mussels (*Dreissena polymorpha*), Environ. Toxicol. Chem. 16:1930-1934(1997).
Crocker, P.J., et al; Development of Agonists, Partial Agonists and Antagonists in the 8-Tetrahydrocannabinol Series, Tetrahedron 55: 13907-13926(1999).
Gau, W., et al; Synthesis of (-)-8-6a, 10a-Trans-Tetrahydrocannabinol, Tetrahedron Lett. 2507-2508 (1972).
Konstantinou, I.K., et al; Worldwide Occurrence and Effects of Antifouling Paint Booster Biocides in the Aquatic Environment: A Review, Environ. Int. 30:235-248 (2004).
Omae, I., General Aspects of Tin-Free Antifouling Paints, Chem. Rev. 103:3431-3448 (2003).
Perry, C., The Habanero of the Harbor, Los Angeles Times, Food Section, Jul. 1, 1993.
Race, T.D., et al; Controlling Zebra Mussels With Coatings, J. Protective Coatings Linings, 60-71, Dec. 1996.
Singer, M., et al; Potent Cyano and Carboxamido Side-Chain Analogues of 1',1'-demethyl-8-tetrahydrocannibol, J. Med. Chem. 41:4400-4407 (1998).
Suedel, B.C., et al; Experimental Factors That May Affect Toxicity of Cadmium to Freshwater Organisms, Arch. Environ. Contam. Toxicol. 33:188-193 (1997).
Walpole, C.S.J., et al; Analogues of Capsaicin With Antagonist Activity as Novel Analgesic Agents: Structure-Activity Studies. 3. The Hydrophobic Side-Chain "C-Region", J. Med. Chem. 36:2381-2389 (1993).
Walsh, M.A., Final Report: Copper-Free Antifouling Coatings, EPA Contract No. 68D03016 (2003).

\* cited by examiner

*Primary Examiner* — Kriellion Sanders
(74) *Attorney, Agent, or Firm* — Jackson Walker L.L.P.

(57) ABSTRACT

Environmentally-friendly alternatives to organometallic antifoulants that are efficacious at preventing biofouling by organisms such as the zebra mussel. Preferred antifoulant compositions utilize compounds having a Lipophilic-Amide-Spacer-ElectroNegative ("LASEN") structural motif, such as capsaicin, and compounds having a TetraHydroCannibinoid ("THC") structural motif. The antifoulant compositions are non-toxic, and effective.

12 Claims, 12 Drawing Sheets

Figure 1

| Cmp | Chemical Name | Chemical Structure | Comments |
|---|---|---|---|
| 1 | Capsaicin (8-Methyl-N-vanillyl-trans-6-nonenamide) purified from a natural product source | | Positive control. Active component of hot sauce. VR1 receptor agonist. |
| 2 | Anandamide (Arachidonylethanolamide) | | Positive control. CB1 and CB2 receptor agonist. |
| 3 | N-vanillylnonanamide | | Pseudocapsaicin: Cheaper synthetic derivative. |
| 4 | D-panthenol | | Alkyldihydroxyl Potential CB2 receptor agonist. |
| 5 | N-(1-(hydroxymethyl)propyl)decanamide | | Shorter alkyl. Interposed ethyl. |
| 6 | N-acetylethanolamine | | No lipophilic portion |
| 7 | N-Boc-ethanolamine | | Short branched alkyl. |
| 8 | Trifluoroethanolamine | | Short bulky lipophilic. |
| 9 | N-Decanoyl-N-methylglucamine | | Shorter alkyl. Multiple hydoxyls. |
| 10 | Natural Product from colleague N-acetylethanolamine (NAE 12:0) | | Short unsaturated chain similar to pseudocapsaicin |
| 11 | N-(4-hydroxy-2-oxo-1,2-dihydro-3-quinolinyl)decanamide | | Shorter alkyl. 2,4,5 electronegative. |

Figure 2

| 12 | N-(2-furylmethyl)decanamide | | Shorter alkyl. Cyclic ether. |
|---|---|---|---|
| 13 | N-benzoylmonoethanolamine benzoate | | Benzyl. Benzoate. |
| 14 | N-(3-acetylphenyl)decanamide | | Shorter alkyl. Acetylbenzyl. |
| 15 | N-(3-nitrophenyl)octadecanamide | | Shorter alkyl. Nitrophenyl. |
| 16 | Stearoyl Ethanolamide | | Endogenous cannabinoid |
| 17 | Linoleyl ethanolamide | | Endogenous cannabinoid |
| 18 | N-(2-(2-(3,4-dimethoxybenzylidene)hydrazine)-2-oxoethyl)dodecanamide | | Does not appear to have "stable" activity |
| 19 | N-oleoylethanolamine | | Endogenous cannabinoid |
| 20 | Oleamide | | Shorter alkyl and No alkylhydroxyl. CB1 receptor agonist. |
| 21 | O-2050 (corrected structure) | | CB1 receptor antagonist. |
| 22 | Noladin ether | | CB1 receptor agonist. |

Figure 3

| 23 | CP 55,940 | | CB1 & CB2 receptor agonist. |
|---|---|---|---|
| 24 | AM630 | | CB2 receptor antagonist. |
| 25 | Palmitylethanolamine | | Shorter alkyl. CB2 receptor agonist. |
| 26 | 2-hydroxy-3-naphthoic acid ethanolamide | | |
| 27 | Olvanil | | Similar to capsaicin |
| 28 | Capsaicin (E-isomer), trans-isomer | | Bioactive isomer at VR1 |
| 29 | Capsaicin (Z-isomer), cis-isomer | | Inactive isomer at VR1 |

| No | Chemical Name | Chemical Structure |
|----|---------------|--------------------|
| 2 | Anandamide (alias: arachidonylethanolamide) N-(2-Hydroxyethyl)-5Z,8Z,11Z,14Z-eicosatetraenamide |  |
| 5 | N-(1-(hydroxymethyl)propyl)decanamide |  |
| 13 | N-benzoylmonoethanolamine benzoate |  |
| 17 | Linoleyl ethanolamide |  |
| 18 | N-(2-(2-(3,4-dimethoxybenzylidene)hydrazine)-2-oxoethyl)dodecanamide |  |
| 21 | O-2050 (6aR,10aR)-3-(1-Methanesulfonylamino-4-hexyn-6-yl)-6a,7,10,10a-tetrahydro-6,6,9-trimethyl-6H-dibenzo [b,d]pyran |  |
| 22 | Noladin ether (aliases: HU 310 and 2-Arachidonyl glycerol ether) 2-[(5Z,8Z,11Z,14Z)-Eicosatetraenyloxy]-1,3-propanediol |  |
| 23 | CP 55,940 (-)-cis-3-[2-Hydroxy-4-(1,1-dimethylheptyl)phenyl]-trans-4-(3-hydroxypropyl)cyclohexanol |  |
| 24 | AM630 6-Iodo-2-methyl-1-[2-(4-morpholinyl)ethyl]-1H-indol-3-yl](4-methoxyphenyl)methanone |  |
| 28 | Capsaicin (E-isomer), trans-isomer (E)-N-[(4-Hydroxy-3-methoxyphenyl)methyl]-8-methyl-6-nonenamide |  |
| 29 | Capsaicin (Z-isomer), cis-isomer (Z)-N-[(4-Hydroxy-3-methoxyphenyl)methyl]-8-methyl-6-nonenamide |  |

ENVIRONMENT-FRIENDLY ANTIFOULANTS FOR THE PREVENTION OF BIOFOULING

This application is a divisional application of and claims priority to, U.S. patent application Ser. No. 12/595,997, now U.S. Pat. No. 8,575,230 entitled "ENVIRONMENT-FRIENDLY ANTIFOULANTS FOR THE PREVENTION OF BIOFOULING," filed on Apr. 16. 2008, which is a 371 application from PCT Application No. PCT/US2008/004891, which claims priority to U.S. Provisional Patent Application Ser. No. 60/925,260, entitled "ENVIRONMENT-FRIENDLY ANTIFOULANTS FOR THE PREVENTION OF BIOFOULING" filed on Apr. 19, 2007, the entire content of each of which is hereby incorporated by reference.

BACKGROUND

This invention pertains to environmentally-friendly alternatives to organometallic antifoulants. These alternatives are efficacious at preventing biofouling by organisms, such as the zebra mussel (*Dreissena polymorpha*), and will minimize overall environmental impact.

Since their introduction into the Great Lakes in the late 1980's, zebra mussel infestations have spread via adjacent interconnected inland waterways and by trailering overland on boat hulls throughout large portions of the United States. Zebra mussels create an expensive biofouling problem by colonizing, and consequently clogging, freshwater intakes so severely that the antifouling costs to U.S. municipal and industrial power generating and water treatment plants is in the billions of dollars, with about 100-400 million dollars being spent annually in the Great Lakes basin alone.

Marine biofouling in general is even more costly, exceeding 5 billion dollars annually. Of major concern is colonization of seafaring vessel hulls by a variety of fouling organisms. This promotes corrosion and increases hydrodynamic drag, which increases fuel consumption and reduces maneuverability. Commercial chemical antifouling methods rely primarily on the use of paints or coatings embedded with copper, tin or zinc, or compounds containing these heavy metals, or combinations of these heavy metals and organic "booster" biocides. However, coatings have a limited lifetime and require periodic re-application, which can be expensive and time consuming. Due to their persistence and the toxicity of their heavy metal components to other aquatic life, such antifouling strategies remain an environmental concern, and legal moratoriums restricting or banning the use of some of these strategies are in place and more are planned. Other antifouling methods include the combined drying and freezing of mussels, which has limited practical applications.

Blending zosteric acid, a known antifoulant isolated from eelgrass (*Zostera marina*) with a coating material has been used to produce an antifoulant coating. However, this antifoulant coating was short-lived and effective for less than 2 months due to hydrolysis of the active component (Walsh M A, 2003).

There have long been case reports by boaters claiming that marine biofouling is significantly reduced when hot sauce containing chili peppers is used as a paint additive (Perry, 1993). The characteristic "hot" sensation experienced when chili peppers are ingested orally is produced by the natural product component capsaicin (8-methyl-N-vanillyl-trans-6-nonenamide). In a controlled laboratory setting, capsaicin has proven to be an effective zebra mussel antifoulant (Cope et al., 1997). However, in initial antifouling field tests, capsaicin was not as effective as copper when simply mixed with paint applied to a surface or when applied to a surface as a dust. (Race and Kelly, 1996).

U.S. Pat. No. 5,629,045 pertains to an anti-fouling composition containing capsaicin in which the capsaicin is mixed with a corrosion resistant epoxy resin and a hardening catalyst and applied to the surface to be protected.

U.S. Pat. No. 5,629,045 pertains to coatings for the prevention of fouling by sea animals which include capsaicin incorporated into standard marine paints, impregnants, and varnishes.

U.S. Pat. No. 6,607,826 pertains to a plastic film applied to the outside of boat hulls or other structures to prevent fouling. Anti-fouling compounds such as capsaicin can be incorporated in the plastic film.

U.S. Patent Application Publication No. 2005/0080160 pertains to paints and coatings containing anti-colonization agents, including capsaicin.

International Patent Application Publication No, 2005/025314 pertains to capsaicin derivatives and their use as micro-organism repellents in paints and coatings.

International Patent Application Publication No. 2005/027642 pertains to repellent preparations containing capsaicin and a wax that can be used as a coating or an additive for paints or plastics.

There still exists a pressing need for new and effective antifouling technologies which are environment-friendly. This "green" technology will potentially result in billions of dollars of savings for both public and private institutions by preventing biofouling in an environmentally sound and responsible manner.

SUMMARY

The present invention relates generally to antifoulants that are relatively non-toxic and environmentally-friendly. These antifoulants are "green" alternatives to current organometallic antifoulants and will minimize overall environmental impact and address the need for a reduction in Persistent Bioaccumulative and Toxic ("PBT") substances.

There have long been case reports by boaters claiming that marine biofouling is significantly reduced when hot sauce containing chili peppers is used as a paint additive. The characteristic "hot" sensation experienced when chili peppers are ingested orally is produced by the natural product component capsaicin (8-methyl-N-vanillyl-trans-6-nonenamide). However, capsaicin is not easily obtained; it is expensive, must be synthesized or isolated from natural sources, and is hazardous to handle. Other environmentally-friendly anti-foulants are more preferred.

Generally, two classes of chemical structures are useful as antifoulants. One has a Lipophilic-Amide-Spacer-ElectroNegative ("LASEN") motif, while the other has a TetraHydro-Cannibinoid ("THC") motif. Particular examples of compounds with the LASEN motif include the natural product capsaicin and related compounds anandamide (arachidonylethanolamide) and pseudocapsaicin (N-vanillylnonanamide). These compounds have reduced toxicity to the target organism (e.g., zebra mussels, *Dreissena polymorpha*) and other non-target organisms (e.g., water fleas, *Daphnia magna*).

The antifoulants of the current invention have been determined to be non-toxic at concentrations that completely prevent biofouling (e.g., $\leq 3 \times 10^{-5}$ M) when dissolved in an aqueous phase.

DETAILED DESCRIPTION OF PREFERRED EMBODIMENTS

One embodiment of the current invention is the Z-isomer of a natural product, capsaicin, that prevents the attachment of zebra mussels to aquatic striatum and that is non-toxic to the target organism at fully efficacious doses. In contrast to stereoisomeric mixtures of capsaicin, the Z-isomer does not act on the vanilloid receptor 1 (VR1) receptor and thus does not give the same "hot" sensation as the E-isomer or of stereoisomeric mixtures containing the E-isomer. This property of the Z-isomer makes it much easier and safer to handle as a raw material, a significant advantage. Surprisingly, it was discovered that the lack of activity at the VR1 receptor did not eliminate the antifoulant activity of stereoisomeric mixtures of capsaicin. Capsaicin (Z-isomer) can be applied as an additive mixed into a paint or polymer coating, impregnated into or slow released (or activity released) from submerged substrates, or it could be added to contained water systems and used as an antifouling treatment (e.g., industrial pipes or ship ballast water). The structures of both compounds are shown below.

Capsaicin (E-isomer)

Capsaicin (Z-isomer)

Additional embodiments of the current invention include classes of compounds that have been demonstrated to be environmentally-friendly antifoulants with enhanced potency or application-specific improved chemical characteristics, such as water solubility and stability. These compounds include some having a Lipophilic-Amide-Spacer-ElectroNegative ("LASEN") structural motif, such as N-vanillyl-nonanamide, capsaicin, anandamide, N-benzoylmono-ethanolamine benzoate, N-(1-hydroxymethyl)propyl) decanamide, linoleyl ethanolamide, and N-(2-(2-(3,4-dimethoxybenzylidene)hydrazine)-2-oxoethyl) dodecanamide. Not all compounds with a LASEN motif are efficacious antifoulants.

Without wanting to be bound by theory, because cannabinoid receptors are a likely target for antifoulants, other compounds having a TetraHydroCannibinoid ("THC") structural motif that are cannabinoid receptor ligands without a LASEN-like structure can also possess antifouling properties. Examples of these compounds include those called O-2050, CP55,940, noladin ether, and AM630. Not all cannabinoid ligands are effective antifoulants. Examples of LASEN and THC compounds are shown below.

LASEN — Anandamide

THC — O-2050

| LASEN | THC |
|---|---|

N-benzoylmonoethanolamine benzoate

CP55,940

Figure 5:
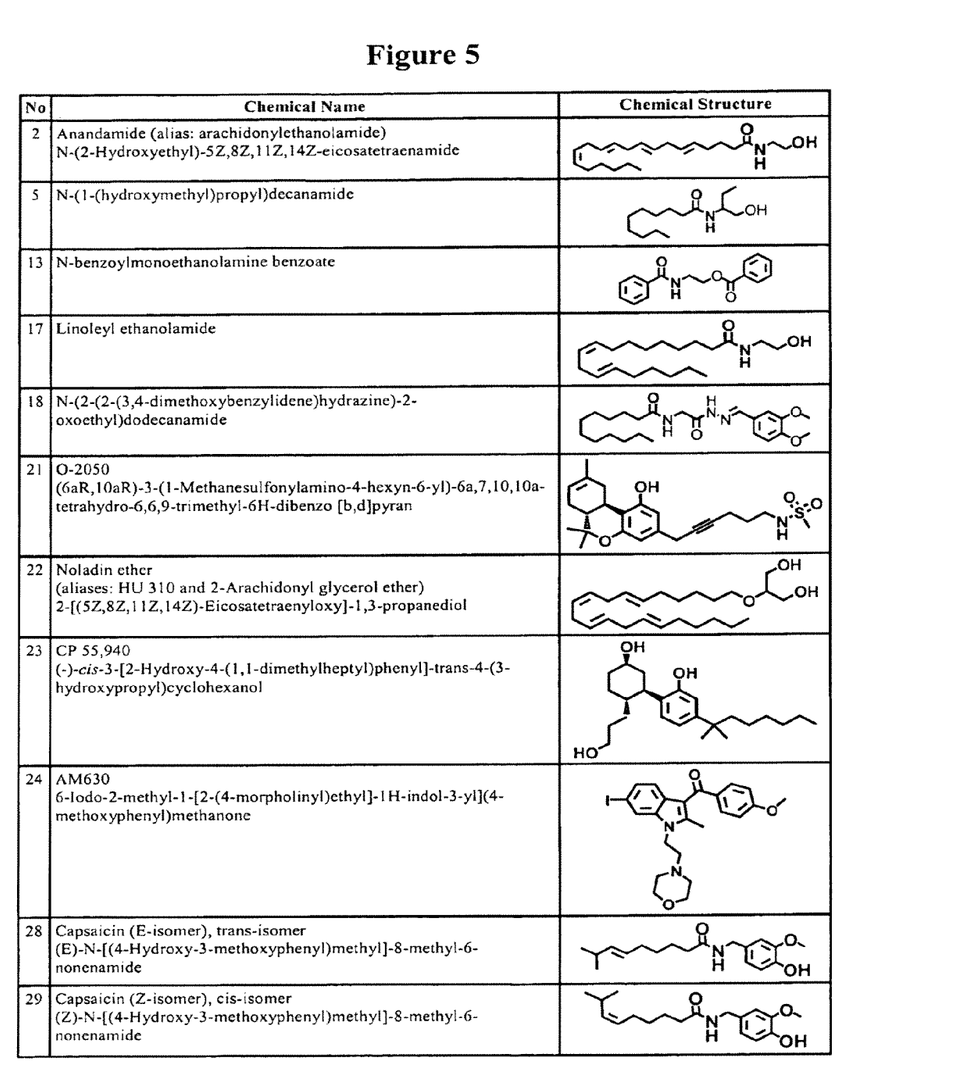
FIG. 5 is a list of select chemicals from FIGS. 1, 2, and 3 that were found to be the most effective antifoulants

Further embodiments of the current invention include various types of compounds, including some having the LASEN and THC structural motifs, and including those shown in FIG. 5, which are shown to be effective, non-toxic, environmentally-friendly antifoulants.

Ideal antifoulants need to have optimal antifouling efficacy, antifouling longevity, minimal toxic liability, and ease of application and cost.

EXAMPLE 1

Antifoulant Activity, Residual Effect, and Toxicity Screening

The antifouling, residual effect and lethal potential of compounds against the prototypical target organisms, zebra mussels, were assessed with a reattachment protocol that was adapted from the original protocol described by Cope et al. (1997). Briefly, fresh stocks of zebra mussels (*Dreissena polymorpha*) were collected and allowed to acclimate in dechlorinated tap water ("DTW"). Mussels of approximately the same length (0.5-1.5 cm) were detached by severing their byssus with a scalpel. For each experimental condition, fifteen detached mussels were placed on their side in a chlorine-free polypropylene dish filled with 200 mL of DTW containing a single high concentration (e.g., 30 µM) of one of the test compounds.

Figure 1:
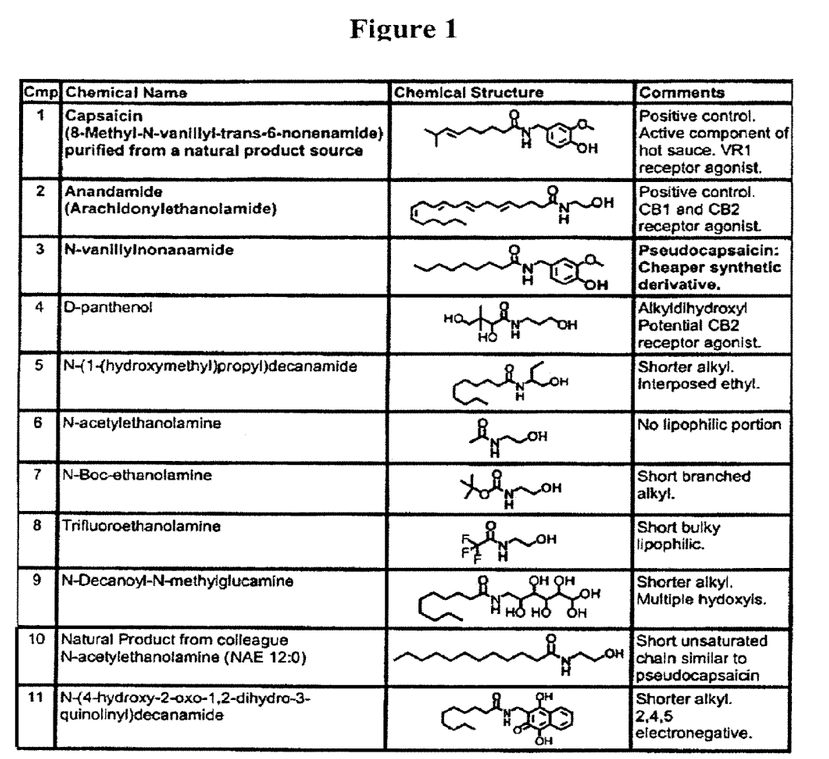
FIG. 1 shows a set of compounds tested for potential antifouling efficacy and non-toxicity (residual effect) against zebra mussels.
Figure 2:
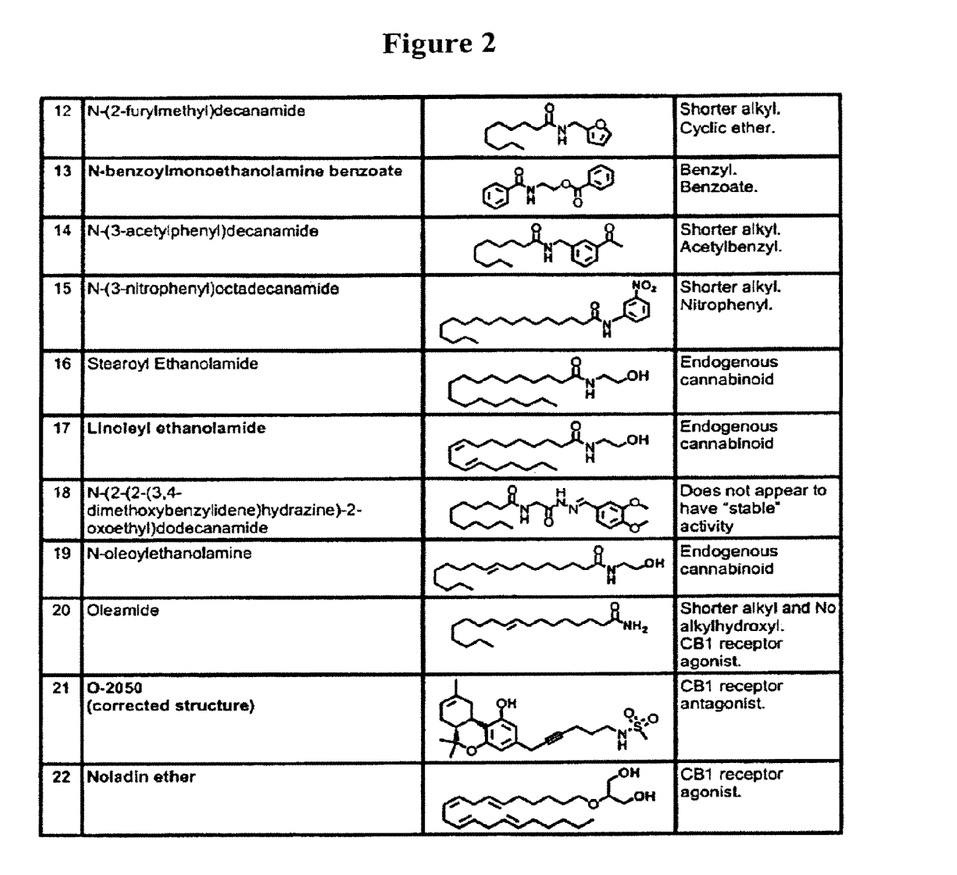
FIG. 2 shows a second set of compounds tested for potential antifouling efficacy and non-toxicity (residual effect) against zebra mussels.
Figure 3:
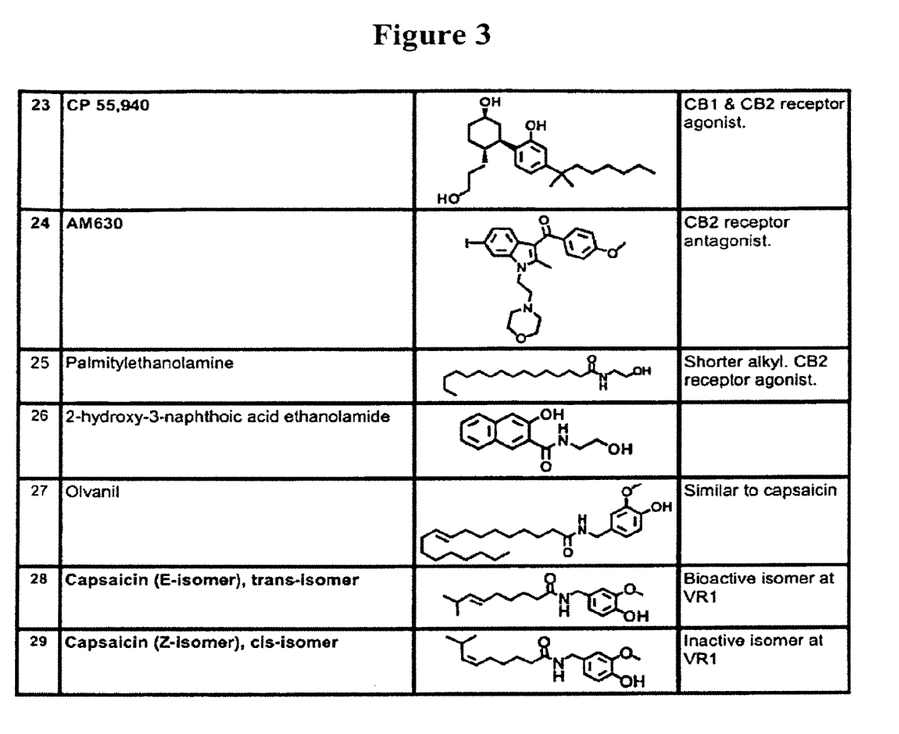
FIG. 3 shows a third set of compounds tested for potential antifouling efficacy and non-toxicity (residual effect) against zebra mussels.

Initial screenings utilized the compounds shown in FIGS. 1, 2, and 3, and in particular anandamide (2), N-(1-(hydroxymethyl)propyl)decanamide (5), N-benzoylmono-ethanolamine benzoate (13), Linoleyl ethanolamide (17). N-(2-(2-(3,4-dimethoxybenzylidene)hydrazine)-2-oxoethyl) dodecanamide, (18), O-2050 (21), noladin ether (22), CP55, 940 (23), AM630 (24), and the E and Z stereoisomers of capsaicin (28 and 29, respectively). A control and several vehicle (solvent) controls were also utilized with the appropriate volume of whatever other non-aqueous solvent that was needed to dissolve the test compounds (e.g., ethanol) at high concentration prior to dilution in DTW.

The animals were housed in an environmental chamber that allowed for ample aeration under conditions of constant temperature and humidity and allowed 48 h to reattach. Reattachment was assessed if the animals produced byssal threads, righted themselves, and were not displaced by pushing on their shells with the tip of a fine paint brush. Those mussels that did not attach within the first 48 h period were transferred to a chamber with fresh DTW, placed on their side and allowed a further 48 h to attach, to measure residual effect. Compounds were considered "toxic" to the mussels, if they failed to attach during this 48 h post-exposure period.

Figure 4:
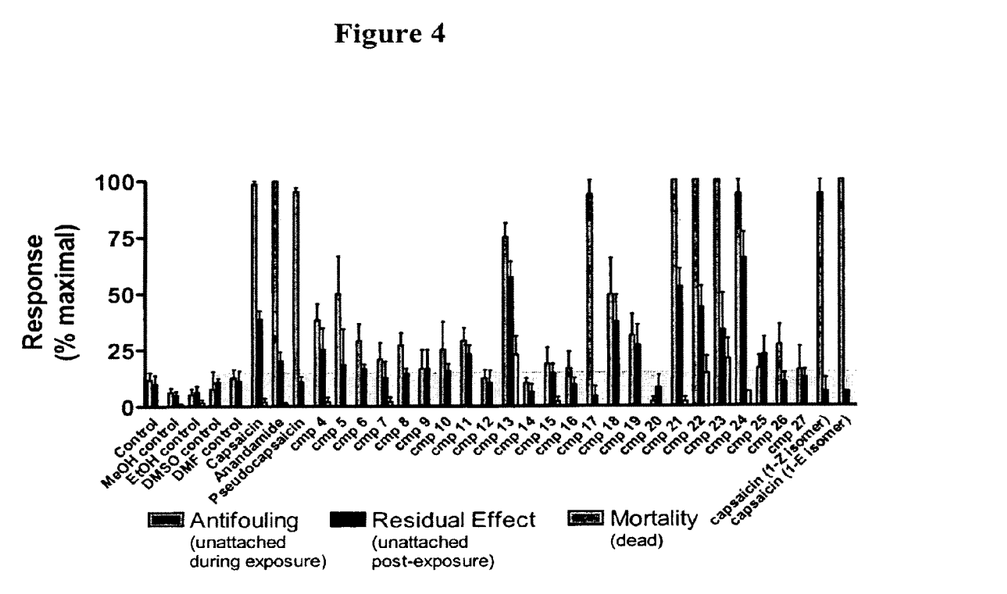
FIG. 4 shows the results of an analysis of the compounds of FIGS. 1, 2, and 3 to determine antifouling efficacy, residual effect, and mortality.
Figure 6:
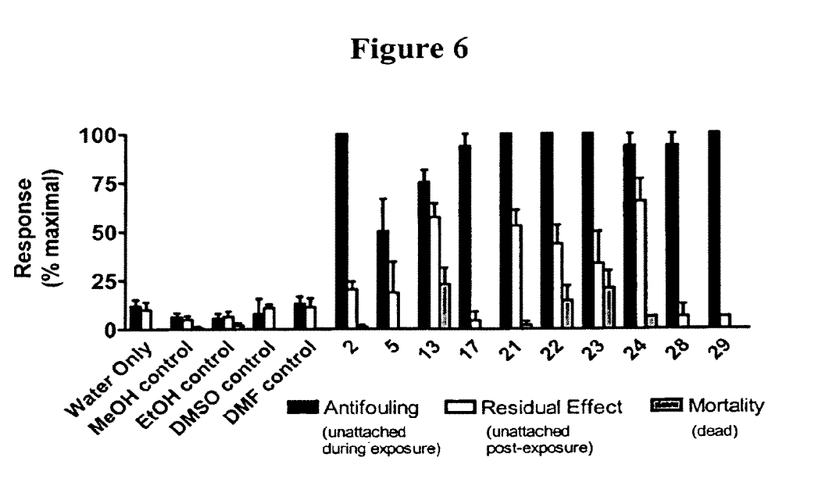
FIG. 6 shows the results of an analysis of the compounds of FIG. 5 to determine antifouling efficacy, residual effect, and mortality.

Each experimental condition was replicated three separate times. The compounds were characterized by efficacy (measured by the fraction of unattached mussels during the first 48 h), residual effect (measured by the fraction of unattached mussels during the second 48 h (post-exposure)), and lethality (measured by the fraction of mussels that died in both periods). The results are shown in FIG. 4 and FIG. 6. Notably, anandamide (2), N-(1-(hydroxymethyl)propyl)decanamide (5), N-benzoylmono-ethanolamine benzoate (13), Linoleyl ethanolamide (17), N-(2-(2-(3,4-dimethoxybenzylidene)hydrazine)-2-oxoethyl)dodecanamide, (18), O-2050 (21), noladin ether (22), CP55,940 (23), AM630 (24), and the E and Z stereoisomers of capsaicin (28 and 29, respectively) were each found to be efficacious antifouling compounds with minimal target organism residual effects ("toxicity") or lethality.

EXAMPLE 2

Antifouling Potency Response Curves

Figure 7:
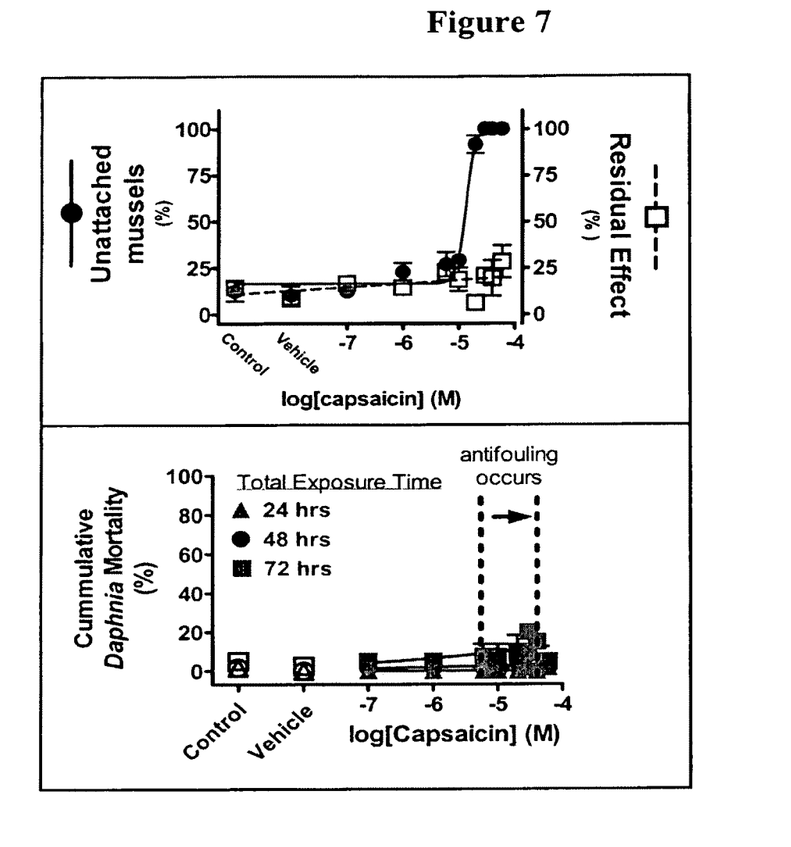
FIG. 7 shows the results of an analysis of the antifouling efficacy and residual effect against zebra mussels (upper panel), and cumulative mortality against non-target organisms (*Daphnia magna*) (lower panel) of capsaicin at different concentrations.
Figure 8:
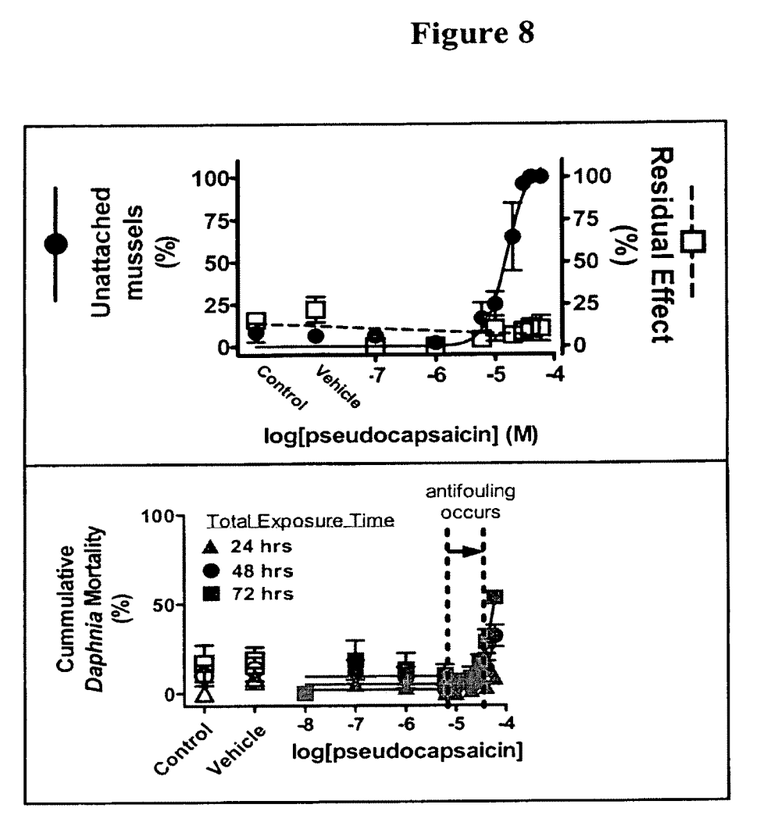
FIG. 8 shows the results of an analysis of the antifouling efficacy and residual effect against zebra mussels (upper panel), and cumulative mortality against non-target organisms (*Daphnia magna*) (lower panel) of pseudocapsaicin (N-vanillylnonanamide) at different concentrations.
Figure 9:
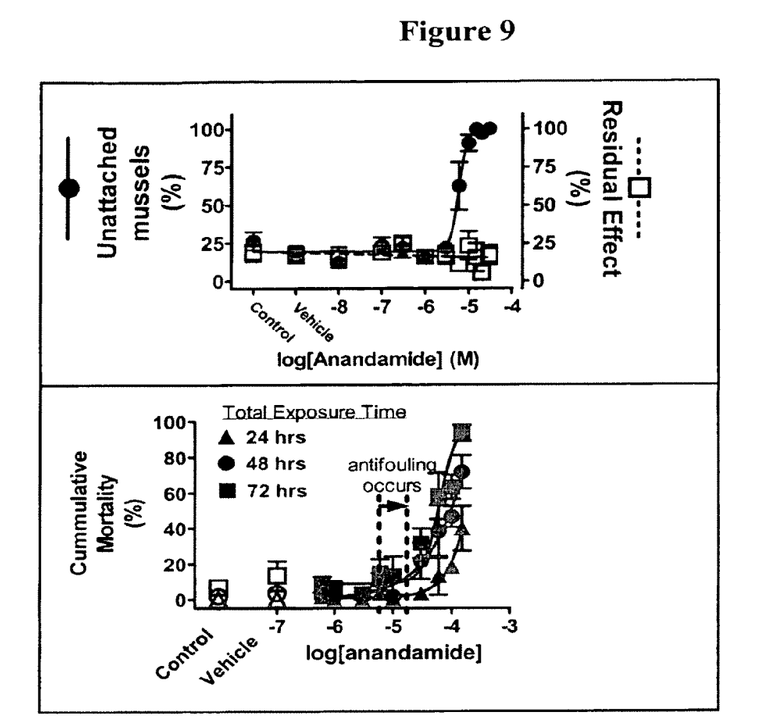
FIG. 9 shows the results of an analysis of the antifouling efficacy and residual effect against zebra mussels (upper panel), and cumulative mortality against non-target organisms (*Daphnia magna*) (lower panel) of anandamide at different concentrations.
Figure 10:
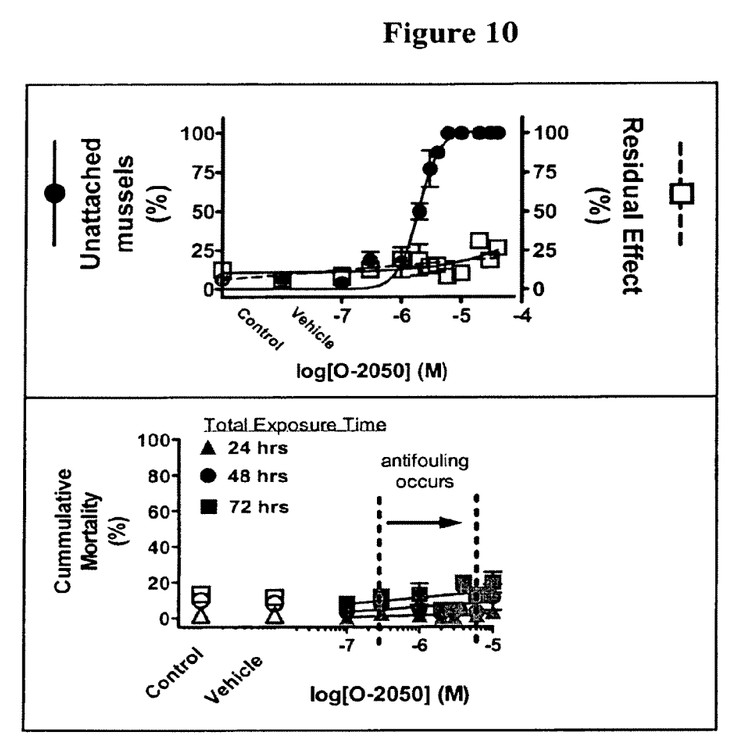
FIG. 10 shows the results of an analysis of the antifouling efficacy and residual effect against zebra mussels (upper panel), and cumulative mortality against non-target organisms (*Daphnia magna*) (lower panel) of O-2050 at different concentrations.
Figure 11:
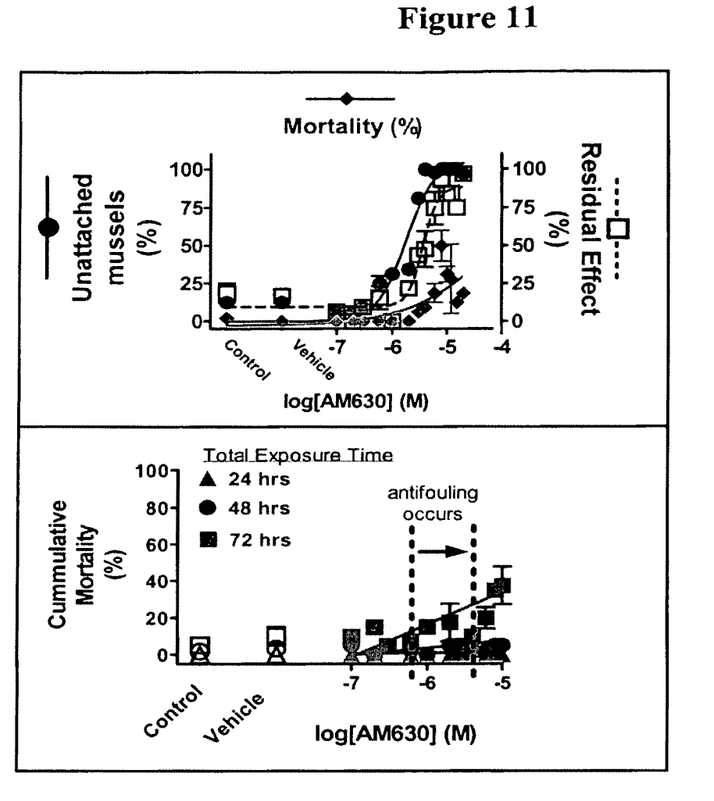
FIG. 11 shows the results of an analysis of the antifouling efficacy and residual effect against zebra mussels (upper panel), and cumulative mortality against non-target organisms (*Daphnia magna*) (lower panel) of AM630 at different concentrations.
Figure 12:
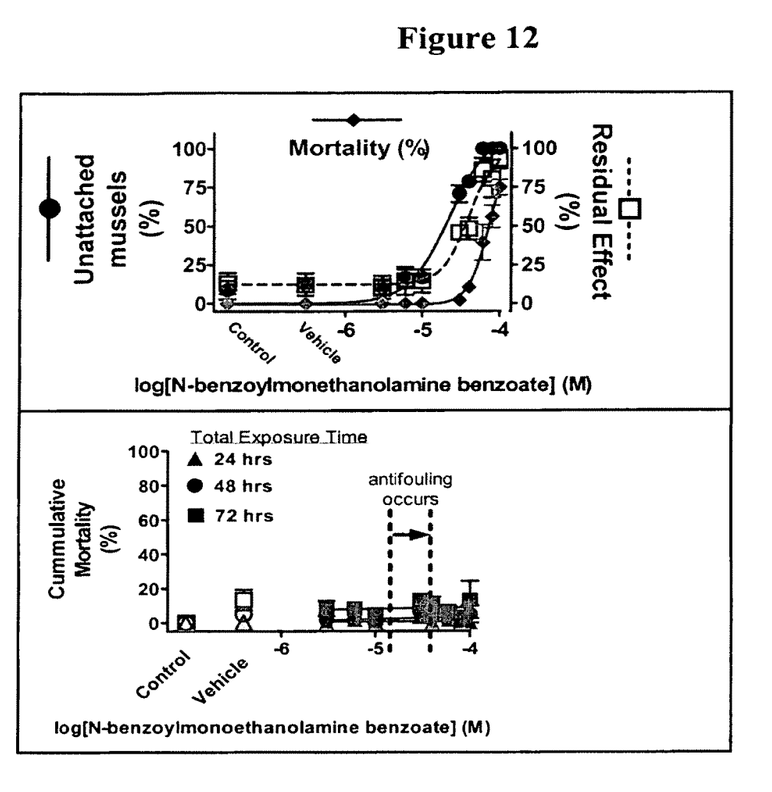
FIG. 12 shows the results of an analysis of the antifouling efficacy and residual effect against zebra mussels (upper panel), and cumulative mortality against non-target organisms (*Daphnia magna*) (lower panel) of N-benzoylmonoethanolamine benzoate at different concentrations.

Some of the compounds displaying the highest maximal antifouling effect (efficacy) at a single high concentration (e.g., 30 µM) and the least toxicity (i.e., largest $LC_{50}$) (FIG. 5) were additionally tested for their potencies ($EC_{50}$). Logistic regression curves were fitted to dose-response data derived from doses spanning at least a three log unit range. The concentration which produces half the maximal effect ($EC_{50}$) is extracted from the regression curves and employed as a comparative measure for refining structure-antifouling relationships. Simultaneous statistical comparisons with a family-wise Type I error rate of alpha=0.05 between these $EC_{50}$'s are achieved via an ANOVA-type analysis and post-hoc pair-wise comparisons using a Boniferri analysis. For example, FIG. 7 shows that capsaicin is an efficacious zebra mussel antifoulant with little residual effect to the target organism. FIG. 8 shows that pseudocapsaicin (N-vanillylnonanamide) is also an efficacious zebra mussel antifoulant with little residual effect. FIG. 8 also shows that pseudocapsaicin (N-vanillylnonanamide) is also not lethal to the non-target organism at a dose that completely prevents mussel biofouling. FIG. 9 shows that anandamide is another efficacious antifoulant with no residual effect. FIG. 10 shows that O-2050 is another efficacious antifoulant with higher potency, with no residual effect at a dose (6 µM) that totally prevents biofouling. FIG. 11 shows that AM630 is another efficacious antifoulant but with some residual effect. FIG. 12 shows that N-benzoylmonoethanolamine benzoate is another efficacious antifoulant but with some residual effect, and a lethal effect against mussel, but not the non-target organism (*Daphnia*). N-benzoylmonoethanolamine benzoate would have utility as a molluscide.

EXAMPLE 3

Non-Target Organism Screening

Those compounds that were determined to be highly efficacious zebra mussel antifoulants with little or no toxicity were additionally assessed for toxicity in another non-target aquatic species. The freshwater cladoceran crustacean *Daphnia magna* (water flea) is commonly utilized for aquatic toxicity testing (Suedel et al., 1997), with 10,583 tests of toxic end points being reported for this species on the USEPA ECOTOX web site. Three replicates of 20 adult specimens of *D. magna* were exposed to each compound employing a dose range that was the same or greater than that used in zebra mussel antifouling studies. The conditions for toxicity testing of water fleas were the same as those used for testing zebra mussel antifouling and toxicity (i.e., polypropylene containers at 15° C.), except that test medium volume was 40 ml and exposure was increased to three days. Dead individuals were removed every 24 h and the total number of surviving individuals was recorded at the end of 1, 2, and 3 days. Although the level of *Daphnia* mortality was too low in most cases, when it was high enough to be reliably estimated then the *Daphnia* lethal dose values (i.e., $LD_{50}$) were estimated using the same methods employed in the mussel byssal attachment studies. Uniformity of test organisms was maintained by establishing a laboratory *D. magna* culture with specimens initially purchased from a biological supply company.

For example, FIG. 8 shows that N-vanillylnonanamide has no significant toxicity towards non-target organisms at a dose that completely prevents mussel biofouling. *Daphnia* cumulative mortality studies indicate that after a 72 h exposure to N-vanillylnonanamide no measurable toxicity over controls occurs at concentrations that produce 100% antifouling (20 and 30 µM). Statistically significant *Daphnia* mortality was only observed at the highest test dose (60 µM) and only at the 72 h time point.

FIG. 9 also shows that anandamide is another efficacious antifoulant with no lethal effect towards a non-target (*Daphnia*) organism at a dose that totally prevents fouling by mussels (15 µM).

FIG. 10 also shows that O-2050 is another efficacious antifoulant with no lethal effect towards a non-target (*Daphnia*) organism at a dose that totally prevents fouling by mussels (6 µM).

FIG. 12 also shows that N-benzoylmonoethanolamine benzoate is another efficacious antifoulant with no toxicity towards a non-target (*Daphnia*) organism at a dose that totally prevents fouling by mussels (60 µM).

FIG. 11 also shows that AM630 is another efficacious antifoulant with no significant lethality towards a non-target (*Daphnia*) organism at a dose that totally prevents fouling by mussels (4 µM)

FIG. 7 shows that racemic capsaicin is another efficacious antifoulant with no toxicity towards a non-target (*Daphnia*) organism at a dose that totally prevents fouling by mussels. This result indicates that neither stereoisomer (E or Z) is toxic towards the non-target (*Daphnia*) organism.

REFERENCES CITED

The following U.S. patent documents and publications are hereby incorporated by reference.

U.S. PATENT DOCUMENTS

U.S. Pat. No. 6,607,826 Hatch
U.S. Pat. No. 6,306,506 Timmons, et al.
U.S. Pat. No. 5,629,045 Veech
U.S. Pat. No. 5,397,385 Watts
International Patent Application Publication No. 2005/0080160
International Patent Application Publication No. 2005/025314
International Patent Application Publication No. 2005/027642

OTHER PUBLICATIONS

Cope, W. G., Bartsch, M. R., Marking, L. L., Efficacy of candidate chemicals for preventing attachment of zebra mussels (*Dreissena polymorpha*), *Environ. Toxicol. Chem.* 16:1930-1934 (1997).
Crocker, P. J., Saha, B., Ryan, W. J., Wiley, J. L., Martin, B. R., Ross, R. A., Pertwee, R. G., Razdan, R. K., Development of Agonists, Partial Agonists and Antagonists in the $\Delta^8$-Tetrahydrocannabinol Series, *Tetrahedron* 55:13907-13926 (1999).
Gau, W., Bieniek, D., Korte, F., Hashish. XXII. Synthesis of (−)-$\Delta^8$-6a, 10a-trans-tetrahydrocannabinol, *Tetrahedron Lett.* 2507-2508 (1972).
Konstantinou I. K., Albanis T. A., Worldwide occurrence and effects of antifouling paint booster biocides in the aquatic environment: a review, *Environ. Int.* 30:235-248 (2004).
Omae, I., General aspects of tin-free antifouling paints, *Chem. Rev.* 103:3431-3448 (2003).
Perry, C., The habanero of the harbor, *Los Angeles Times*, Food Section, Jul. 1, 1993.
Race, T. D., Kelly, M. A., Controlling Zebra mussels with coatings, *J. Protective Coatings Linings*, December, 60-71 (1996).
Singer, M., Ryan, W. J., Saha, B., Martin, B. R., Razdan, R. K., Potent Cyano and Carboxamido Side-Chain Analogues of 1′,1′-Dimethyl-$\Delta^8$-tetrahydrocannibol, *J. Med. Chem.* 41:4400-4407(\998).
Suedel, B. C., Rodgers, Jr., J. H., Deaver, E., Experimental factors that may affect toxicity of cadmium to freshwater organisms, *Arch. Environ. Contain. Toxicol.* 33:188-193 (1997).
Walpole, C. S. J., Wrigglesworth, R., Bevan, S., Campbell, E. A., Dray, A., James, I. F., Masdin, K. J., Perkins, M. N., Winter, J., Analogues of Capsaicin with Antagonist Activity as Novel Analgesic Agents: Structure-Activity Studies. 3. The Hydrophobic Side-Chain "C-Region," *J. Med. Chem.* 36: 2381-2389 (1993).
Walsh, M. A., Final Report: Copper-free antifouling coatings, EPA Contract Number 68D03016 (2003).

What is claimed is:
1. An antifoulant composition comprising:
(a) N-(2-(2-(3,4-dimethoxybenzylidene)hydrazine)-2-oxoethyl)dodecanamide, having the structure:

(b) anandamide, having the structure:

(c) N-benzoylmonoethanolamine benzoate, having the structure:

(d) N-(1-(hydroxymethyl)propyl)decanamide, having the structure:

or (e) Linoleyl ethanolamide, having the structure:

wherein the composition is effective at reducing aquatic biofouling on a surface after application to the surface or addition of the composition to the aquatic environment in contact with the surface.

2. The antifoulant composition of claim 1, further comprising a polymer, wherein the compound is mixed with the polymer to form a blended mixture.

3. The antifoulant composition of claim 1, further comprising a paint, wherein the compound is mixed with the paint to form a blended mixture.

4. The antifoulant composition of claim 1, further comprising a coating, wherein the compound is mixed with the coating to form a blended mixture.

5. An antifoulant composition comprising:
a compound having a Tetra-HydroCannibinoid ("THC") structure,
wherein the composition is effective at reducing aquatic biofouling on a surface after application to the surface or addition of the composition to the aquatic environment in contact with the surface.

6. An antifoulant composition comprising:
(a) O-2050, having the structure:

(b) CP55,940, having the structure:

(c) Noladin ether, having the structure:

or
(d) AM630, having the structure:

wherein the composition is effective at reducing aquatic biofouling on a surface after application to the surface or addition of the composition to the aquatic environment in contact with the surface.

7. The antifoulant composition of claim 6, further comprising a polymer, wherein the compound is mixed with the polymer to form a blended mixture.

8. The antifoulant composition of claim 6, further comprising a paint, wherein the compound is mixed with the paint to form a blended mixture.

9. The antifoulant composition of claim 6, further comprising a coating, wherein the compound is mixed with the coating to form a blended mixture.

10. A method of treating contained water systems to reduce aquatic biofouling on inner surfaces of the contained water systems comprising:
   contacting the composition of claim 1 with the inner surfaces of the contained water system.

11. A method of treating contained water systems to reduce aquatic biofouling on inner surfaces of the contained water systems comprising:
   contacting the composition of claim 6 with the inner surfaces of the contained water system.

12. A method of treating contained water systems to reduce aquatic biofouling on inner surfaces of the contained water systems comprising:
   contacting an antifoulant compound with the inner surfaces of the contained water system, wherein the antifoulant compound comprises:
   (a) AM630, having the structure:

(b) anandamide, having the structure:

(c) N-benzoylmonoethanolamine benzoate, having the structure:

(d) N-(1(hydroxymethyl)propyl)decanamide, having the structure:

(e) Linoleyl ethanolamide, having the structure:

N-(2-(2-(3,4-dimethoxybenzylidene)hydrazine)2-oxoethyl)dodecanamide, having the structure:

(g) O-2050, having the structure:

(h) CP55,940, having the structure:

or (i) Noladin ether, having the structure:

* * * * *